(12) United States Patent
Sasaki et al.

(10) Patent No.: US 11,207,448 B2
(45) Date of Patent: Dec. 28, 2021

(54) BIOABSORBABLE STENT

(71) Applicants: Japan Medical Device Technology Co., Ltd., Kumamoto (JP); National University Corporation Kumamoto University, Kumamoto (JP)

(72) Inventors: Makoto Sasaki, Kumamoto (JP); Takuro Niidome, Kumamoto (JP); Zhen Yu Jin, Kumamoto (JP); Shuzo Yamashita, Kumamoto (JP)

(73) Assignees: JAPAN MEDICAL DEVICE TECHNOLOGY CO., LTD., Kumamoto (JP); NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 400 days.

(21) Appl. No.: 15/988,482

(22) Filed: May 24, 2018

(65) Prior Publication Data

US 2018/0264180 A1 Sep. 20, 2018

Related U.S. Application Data

(63) Continuation of application No. PCT/JP2016/085038, filed on Nov. 25, 2016.

(30) Foreign Application Priority Data

Nov. 26, 2015 (JP) ............................. JP2015-231163

(51) Int. Cl.
*A61F 2/915* (2013.01)
*A61L 31/14* (2006.01)
(Continued)

(52) U.S. Cl.
CPC .............. *A61L 31/148* (2013.01); *A61F 2/90* (2013.01); *A61F 2/915* (2013.01); *A61L 31/022* (2013.01);
(Continued)

(58) Field of Classification Search
None
See application file for complete search history.

(56) References Cited

U.S. PATENT DOCUMENTS

| 5,464,650 A | 11/1995 | Berg et al. |
| 5,624,411 A | 4/1997 | Tuch |

(Continued)

FOREIGN PATENT DOCUMENTS

| CN | 101795719 | 8/2010 |
| CN | 103876869 | 6/2014 |

(Continued)

OTHER PUBLICATIONS

Chinese Office Action dated Feb. 26, 2020 in corresponding Chinese Patent Application No. 201680069168.5 (25 pages).

(Continued)

*Primary Examiner* — Megan Y Wolf

(57) ABSTRACT

Provided is a biodegradable polymer coating stent effective in delaying the damage of physical properties (particularly radial force) of a core structure. The stent includes a core structure of a bioabsorbable material (e.g., Mg), a first coating layer of a first polymer with biodegradability, and a second coating layer of a second polymer with biodegradability, wherein the first coating layer covers the whole surface of the core structure; the second coating layer covers a part or the whole surface of the first coating layer; the first polymer has a glass transition point of lower than 37° C.; and the second polymer has a glass transition point of 47° C. or higher.

10 Claims, 5 Drawing Sheets

(51) Int. Cl.
  *A61F 2/90* (2013.01)
  *A61L 31/02* (2006.01)
  *A61L 31/10* (2006.01)
  *A61L 31/16* (2006.01)

(52) U.S. Cl.
  CPC .............. *A61L 31/10* (2013.01); *A61L 31/14* (2013.01); *A61L 31/16* (2013.01); *A61F 2002/91558* (2013.01); *A61F 2210/0004* (2013.01); *A61F 2210/0076* (2013.01); *A61F 2240/001* (2013.01); *A61F 2250/003* (2013.01); *A61F 2250/0046* (2013.01); *A61L 2300/416* (2013.01); *A61L 2300/42* (2013.01); *A61L 2300/608* (2013.01); *A61L 2420/08* (2013.01)

(56) References Cited

U.S. PATENT DOCUMENTS

| | | | |
|---|---|---|---|
| 5,679,400 A | 10/1997 | Tuch | |
| 5,776,184 A | 7/1998 | Tuch | |
| 5,824,048 A | 10/1998 | Tuch | |
| 5,837,008 A | 11/1998 | Berg et al. | |
| 6,045,568 A | 4/2000 | Igaki et al. | |
| 6,080,177 A | 6/2000 | Igaki et al. | |
| RE38,653 E | 11/2004 | Igaki et al. | |
| RE38,711 E | 3/2005 | Igaki et al. | |
| 6,997,949 B2 | 2/2006 | Tuch | |
| 7,419,696 B2 | 9/2008 | Berg et al. | |
| 7,698,111 B2 | 4/2010 | Abrahao et al. | |
| 7,811,317 B2 | 10/2010 | Berg et al. | |
| 8,088,060 B2 | 1/2012 | Cottone, Jr. et al. | |
| 8,409,272 B2 | 4/2013 | Omura et al. | |
| 8,460,367 B2 | 6/2013 | Cottone, Jr. et al. | |
| 8,641,756 B2 | 2/2014 | Omura et al. | |
| 8,889,823 B2 | 11/2014 | Wang et al. | |
| 8,968,392 B2 | 3/2015 | Omura et al. | |
| 9,040,111 B2 | 5/2015 | Omura et al. | |
| 9,248,218 B2 | 2/2016 | Wang et al. | |
| 9,283,304 B2 | 3/2016 | Zhao | |
| 9,320,829 B2 | 4/2016 | Cottone, Jr. et al. | |
| 9,474,637 B2 | 10/2016 | Zhao | |
| 9,687,594 B2 | 6/2017 | Wang et al. | |
| 9,821,093 B2 | 11/2017 | Cottone, Jr. et al. | |
| 9,844,612 B2 | 12/2017 | Wang et al. | |
| 9,889,238 B2 | 2/2018 | Wang et al. | |
| 2002/0005571 A1 | 5/2002 | Tuch | |
| 2002/0138048 A1 | 9/2002 | Tuch | |
| 2003/0176914 A1* | 9/2003 | Rabkin | A61F 2/915 623/1.15 |
| 2005/0238686 A1* | 10/2005 | Hossainy | A61L 31/10 424/423 |
| 2005/0271701 A1 | 12/2005 | Cottone, Jr. et al. | |
| 2006/0085064 A1 | 4/2006 | Tuch | |
| 2006/0224531 A1 | 10/2006 | Abrahao et al. | |
| 2007/0123977 A1 | 5/2007 | Cottone, Jr. et al. | |
| 2007/0128723 A1 | 6/2007 | Cottone, Jr. et al. | |
| 2007/0129789 A1 | 6/2007 | Cottone, Jr. et al. | |
| 2007/0135908 A1 | 6/2007 | Zhao | |
| 2007/0141107 A1 | 6/2007 | Kutryk et al. | |
| 2008/0051871 A1 | 2/2008 | Tuch | |
| 2008/0275544 A1 | 11/2008 | Berg et al. | |
| 2009/0240323 A1 | 9/2009 | Wilcox | |
| 2010/0131050 A1 | 5/2010 | Zhao | |
| 2010/0198344 A1 | 8/2010 | Omura et al. | |
| 2010/0249914 A1 | 9/2010 | Omura et al. | |
| 2010/0262228 A1 | 10/2010 | Udipi et al. | |
| 2010/0305689 A1 | 12/2010 | Venkatraman et al. | |
| 2010/0323093 A1* | 12/2010 | Chen | A61F 2/86 427/2.25 |
| 2011/0021717 A1 | 1/2011 | Wang et al. | |
| 2011/0022155 A1 | 1/2011 | Wang et al. | |
| 2012/0172970 A1 | 7/2012 | Cottone, Jr. et al. | |
| 2012/0172974 A1* | 7/2012 | Feng | A61F 2/915 623/1.16 |
| 2012/0310329 A1 | 12/2012 | Omura et al. | |
| 2013/0018455 A1 | 1/2013 | Omura et al. | |
| 2013/0115363 A1 | 5/2013 | Omura et al. | |
| 2013/0131778 A1 | 5/2013 | Igaki et al. | |
| 2013/0295156 A1 | 11/2013 | Cottone, Jr. et al. | |
| 2014/0277379 A1 | 9/2014 | Vogel et al. | |
| 2015/0057744 A1 | 2/2015 | Wang et al. | |
| 2016/0101222 A1 | 4/2016 | Wang et al. | |
| 2016/0136337 A1 | 5/2016 | Cottone, Jr. et al. | |
| 2016/0184114 A1 | 6/2016 | Cottone, Jr. | |
| 2016/0262916 A1 | 9/2016 | Zhao | |
| 2016/0287708 A9 | 10/2016 | Cottone, Jr. et al. | |
| 2017/0095358 A1* | 4/2017 | Savage | A61L 31/148 |
| 2017/0252493 A1 | 9/2017 | Wang et al. | |
| 2018/0036118 A1 | 2/2018 | Cottone et al. | |
| 2018/0185131 A1* | 7/2018 | Allen | A61F 2/06 |

FOREIGN PATENT DOCUMENTS

| | | |
|---|---|---|
| CN | 104013996 A | 9/2014 |
| CN | 105078631 | 11/2015 |
| JP | 8-33718 | 2/1996 |
| JP | 9-56807 | 3/1997 |
| JP | 2842943 | 10/1998 |
| JP | 4340744 | 7/2009 |
| JP | 2010-178958 | 8/2010 |
| JP | 5425364 | 12/2013 |
| JP | 5701497 | 2/2015 |
| JP | 2015-154925 | 8/2015 |
| JP | 2015-154957 | 8/2015 |
| WO | 2007/059253 A2 | 5/2007 |
| WO | WO 2009/117241 A2 | 9/2009 |
| WO | WO 2015/147184 A1 | 10/2015 |

OTHER PUBLICATIONS

Communication pursuant to Article 94(3) EPC dated Mar. 17, 2020 in corresponding European Patent Application No. 16868690.5 (6 pages).
Chinese Office Action dated Jun. 19, 2020, in corresponding Chinese Patent Application No. 201680069168.5.
International Preliminary Report on Patentability dated Jun. 7, 2018 in corresponding International Patent Application No. PCT/JP2016/085038, 9 pgs.
English Abstract for International Patent Publication No. WO 92/15342, published Sep. 17, 1992.
International Search Report dated Feb. 7, 2017 in corresponding International Patent Publication No. PCT/JP2016/085038.
Extended European Search Report dated Jun. 25, 2019 in corresponding European Patent Application No. 16868690.5.
Japanese Office Action dated Jul. 9, 2019 in corresponding Japanese Patent Application No. 2017-552741.
Chinese Office Action dated Jun. 3, 2019 in corresponding Chinese Patent Application No. 201680069168.5.
Reasons for Refusal dated Jan. 8, 2019 in corresponding Japanese Patent Application No. 2017-552741, 4 pages.
Examination Report dated Oct. 3, 2020, in Australian Patent Application No. 2016361380 (four pages).
Examination Report dated Oct. 28, 2020, in Indian Patent Application No. 201817020057 (six pages).

* cited by examiner

BIOABSORBABLE STENT

CROSS REFERENCE TO THE RELATED APPLICATION

This application is a continuation application, under 35 U.S.C.§ 111(a), of international application No. PCT/JP2016/085038, filed Nov. 25, 2016, which claims priority to Japanese patent application No. 2015-231163, filed Nov. 26, 2015, the entire disclosure of which is herein incorporated by reference as a part of this application.

FIELD OF THE INVENTION

The present invention relates to a bioabsorbable stent that is implanted in a stenosis part or an occlusion part in lumen of living body so as to keep the inserted part open, and further to a bioabsorbable stent that is gradually degraded in the living body.

BACKGROUND ART

In recent years, due to westernization of lifestyle as well as aging, arteriosclerotic diseases, such as myocardial infarction, angina, apoplexy, and peripheral vessel disease, have been increasing more and more in our country. As one of the reliable cure to such arteriosclerotic diseases, for example, there is mentioned endermic intervention, which makes the stenosis part or occlusion part of a blood vessel open, represented by a percutaneous transluminal coronary angioplasty (hereinafter referred to as PTCA) in the coronary arteries of the heart. In connection with the technical innovation of applicable medical instruments, the PTCA has been prevailing generally and widely as a cure excellent in QOL and economic efficiency.

The PTCA is a procedure for recovering blood flow by inserting a thin tube (catheter) with a balloon at an end of the tube from an artery in arm or thigh, passing the tube to a stenosis part of the heart coronary artery, and then inflating the balloon so as to expand the stenosis part of the blood vessel. Thereby, the intravascular lumen of the lesion part is enlarged so that the amount of the blood flow passing along the intravascular lumen is increased.

However, if a blood vessel wall is damaged by the catheter, the damage causes a recovery reaction of the blood vessel wall so as to cause propagation of the intima of the vessel. Accordingly, about 10% of the PTCAs which successfully enlarged the crown strangulation lesion part have still needed retreatment. Since it is necessary to carry out another PTCA where a restenosis arises, establishment of the prevention method and improved cure serves as urgent requirement.

In recent years, medical instruments called stent have been used. The stent is placed in a stenosis part in lumina, such as a blood vessel, a tracheal gill, an esophagus, and a urethra, so as to keep the part open. There are two types of stent, a self-expanding stent and a balloon-expanding stent. The self-expanding stent is first folded up into a small contracted state and inserted into a target part, and then the stress which maintains contraction of the folded stent is removed to make the stent enlarged radially due to the resilience of the stent itself so as to be fixed on the inside of the biological organ. The balloon-expanding stent is enlarged by expansive force of a balloon positioned inside the stent. However, as far as it goes, the restenosis cannot be fully suppressed only by placing a stent in the stenosis part.

In general, vascular damages have occurred at the part subjected to the PTCA or the stent placement by injury such as exfoliation of vascular endothelial cells or damage to elastic membranes. It is thought that healing response of a living body to these injuries has comparatively continued for a long period of time (for about two months after stent placement). More specifically, it is thought that the restenosis in humans is mainly caused by inflammation process in adhesion of the monocyte and/or infiltration which arises at 1 to 3 days after the PTCA or stent placement; and by intimal thickening process by smooth muscle cells showing the highest fecundity at about 45 days after the PTCA or stent placement.

In order to solve these problems, there has been employed a drug-eluting stent in which the stent made of a metal or a polymer material is provided with a surface layer carrying an anti-inflammatory agent and a growth inhibiter of smooth muscle cells (Patent Document 1 and Patent Document 2).

There has been proposed a stent with a stent body comprising a bioabsorbable material. For example, there has been proposed an angiogenic stent comprising a knit cylindrical or tubular structure made of fibers of a bioabsorbable polymer (polylactic acid) has been proposed (Patent Document 3).

In general, where a bare metal stent comprising as a base material a bioabsorbable magnesium alloy is uniformly polished by electrolytic polishing, and then is expanded in an aqueous solution, corrosion of the stent advances throughout the surface on which water molecules are brought into contact so that the mechanical strength (physical properties) of the stent is gradually spoiled. In order to prevent such a corrosion, there is an attempt that the base material surface is coated with a biodegradable polymer so that the coated surface functions as a barrier to impede contact with water molecules (Patent Documents 5 and 6).

The stents described in Patent Document 1 and Patent Document 2 can achieve drastic reduction in restenosis rate, because the medicine can be locally eluted over a long period of time in the detention part of the lumen. However, since these stent bodies are formed of metallic material, the stents will be placed semi-permanently in the living body. As a result, after the medicine has been completely eluted, there is a possibility that chronic inflammation resulting from the mechanical stress of the stent bodies to the blood vessel wall may happen. Accordingly, a stent comprising a stent body of a bioabsorbable material has been proposed as a stent which solves the above-mentioned problem of metal stents.

The stent comprising the bioabsorbable polymer described in Patent Document 3 has a problem that such a stent is weaker in strength than metal stents, resulting in insufficient bearing power, i.e., radial force of blood vessel. Even if the bioabsorbable polymer stent would achieve a radial force equivalent to the metal stent by enlarging thickness, such a stent is not practical because of increased rate of restenosis (it is important that the stent should have a thickness of 130 µm or smaller according to the past clinical results in order to reduce mitigation of the restenosis rate) as well as deterioration in delivery of the stent to the affected part.

Magnesium alloy described in Patent Document 4 has higher strength compared with bioabsorbable polymers so that the magnesium alloy can realize practical stent thickness. However, since the degradation (corrosion) rate of the bioabsorbable magnesium alloy in the living body is very fast, such a stent has a problem, considering the demand that the stent be placed in the body for a predetermined period, with securing sufficient blood vessel bearing power (radial force) at least for about six months after stent placement.

These attempts described in Patent Document 5 and Patent Document 6 should have suppressed the rise of pH caused by corrosion of magnesium alloy, but such attempts sometimes have ended up fatal damage in physical properties (particularly radial force) of the stent body. These attempts rather cause local intensive and accelerative corrosion (local corrosion) because of microscopic cavities (FIG. 1) generated in the interface between the stent body and the polymer by stent expansion, and cracks (FIG. 2) of the coating layer at the stress risers (stress concentration area). The cavities problematically cause local pH rise accompanied by stay of corrosion products, such as magnesium hydroxide and hydrogen gas. On the other hand, it is thought that the uneven surface due to the cracks can serve as a trigger of pitting corrosion (local corrosion).

As far as the medical devices perform plastic elastic deformation (physical change) by crimping the devices (diameter reduction) to be installed in a balloon catheter, or stenting the devices (diameter expansion), it is extremely difficult to simultaneously avoid phenomena such as a cavity and a crack. For example, when there is no crack at a stress riser during diameter reduction and diameter expansion of a stent coated with a polylactic acid, it may be interpreted that the stent effectively improves corrosion-resistance. However, in fact, as shown in FIG. 1, due to physical change of the stent caused by diameter reduction as well as diameter expansion, the polymer layer 2 on the base material (core structure) 1 comes apart from the surface of the base material 1, resulting in chaotic occurrence of highly sealed cavities 3 at the interface between the base material and polymer layer. As described above, in connection with the local corrosion due to the local pH rise, such a phenomenon brings about fatal damage to physical properties (particularly radial force) of the base material. That is, the surface of the base material completely covered with polylactic acid serves as a stay place of the corrosion product. Optimization of the molecular weight of the polylactic acid as well as the thickness of the coating layer cannot fundamentally resolve this problem. Thus, as for the stents with physical change, the approach of adjusting pH environment as described above in Patent Documents 5 and 6 is not effective.

RELATED ART DOCUMENT

Patent Document

[Patent document 1] JP Laid-open Patent Publication No. 8-33718
[Patent document 2] JP Laid-open Patent Publication No. 9-56807
[Patent document 3] JP Patent No. 2842943
[Patent document 4] JP Patent No. 4340744
[Patent document 5] JP Patent No. 5425364
[Patent document 6] JP Patent No. 5701497

SUMMARY OF THE INVENTION

Problems to be Solved by the Invention

An object of the present invention is to provide a stent having a biodegradable polymer coating layer, where the stent can effectively retard damage in physical properties (particularly radial force) of a bioabsorbable material which forms a core structure of the stent, particularly a bioabsorbable magnesium alloy core structure, and can sustain physical properties in the simulated plasma solution (EMEM+ 10% FBS) at 37° C. under 5% $CO_2$ atmosphere over one month.

Means for Solving the Problems

In order to solve the above-mentioned problems, the inventors have made eager investigations on retardation in physical damage of bioabsorbable material (especially bioabsorbable magnesium alloy) which forms a core structure, and have found out that: if a core structure of a stent has a two-layer coating structure comprising two layers each comprising a biodegradable polymer having a glass transition point being different from each other, such a stent can effectively deter occurrence of cavities at a core structure-polymer interface, and occurrence of cracks in the polymer coating layer during stent expansion, as well as can effectively delay weight loss and physical damage (particularly radial force) of the core structure. Thus, the present invention has been accomplished.

According to a first aspect of a present invention, a stent comprises a core structure of a bioabsorbable material, a first coating layer of a biodegradable polymer (a first polymer), and a second coating layer of a biodegradable polymer (a second polymer), wherein the first coating layer covers the whole surface of the core structure tightly; the second coating layer covers a part or the whole surface of the first coating layer; the first polymer has a glass transition point (Tg) of lower than 37° C.; and the second polymer has a Tg of 47° C. or higher. Thus, it is necessary that difference in Tg between the first polymer and the second polymer is at least 10° C. or greater (preferably 20° C. or greater, still more preferably 30° C. or greater). In this case, crystalline nature of each of the first polymer and the second polymer is not limited to a specific one, and may be either semicrystalline or crystalline. (Crystallinity refers to a degree of regular arrangement of polymer chains.) For example, an aggregate comprising single species of polymer chains has excellent crystallinity.

In a second aspect of the present invention, according to the first aspect, the bioabsorbable material may preferably comprise a magnesium alloy containing at least one member selected from the group consisting of Li, Ca, Ti, V, Cr, Mn, Fe, Zn, Zr, Nb, or Ta; may more preferably comprise a magnesium alloy excluding aluminum; and may further preferably comprise a magnesium alloy excluding rare earth (excluding any of Sc, Y, Dy, Sm, Ce, Gd, or La).

In a third aspect of the present invention, according to the first or second aspect, each of the first coating layer and the second coating layer has a film thickness of from 1 to 5 and further the total film thickness of the two layers is 2 μm or larger, and 10 μm or smaller.

In a forth aspect of the present invention, according to any one of the first to the third aspects, the second coating layer of the second polymer may contain an intimal thickening inhibitor.

In a sixth aspect of the present invention, according to any one of the first to fifth aspects, each of the first polymer and the second polymer preferably has a number average molecular weight of 30000 g/mol to 200000 g/mol.

In a sixth aspect of the present invention, according to any one of the first to fifth aspects, each of the first polymer and the second polymer preferably has a number average molecular weight of 30000 to 200000.

In a seventh aspect of the present invention, according to any one of the first to sixth aspects, the preferably combinations of the first polymer and the second polymer (first polymer/second polymer) include, as combinations of first polymer/second polymer, PCL (−65° C.≤Tg≤−60° C.)/PDLLA (50° C.≤Tg≤55° C.); PLCL (−60° C.≤Tg≤37° C.)/PDLLA (50° C.≤Tg≤55° C.); PCL (−65° C.≤Tg≤−60° C.)/PLLA (60° C.≤Tg≤65° C.); or PLCL (−60° C.≤Tg≤37° C.)/PLLA (60° C.≤Tg≤65° C.).

In the seventh aspect, the first polymer may be preferably a poly(ε-caprolactone) (PCL), a poly(lactic acid-ε-caprolactone) (PLCL).

The second polymer may be preferably a poly(L-lactic acid) (PLLA), a poly(D, L-lactic acid) (PDLLA). The PDLLA is not limited to have a specific polymer structure, and may be either a block copolymer or a random copolymer. The copolymerization ratio of D-lactic acid and L-lactic acid is not limited to a specific one.

In an eighth aspect of the present invention, according to the seventh aspect, the PLCL is not limited to a specific polymer, and may be either a block copolymer or a random copolymer, but the copolymerization ratio of caprolactone is preferably 20 mol % or higher.

In a ninth aspect of the present invention, according to any one of the first to eighth aspects, the core structure of the bioabsorbable material is preferably capable of maintaining the radial force over one month in the simulated plasma solution (EMEM+10% FBS) at 37° C. under 5% $CO_2$ atmosphere.

In a tenth aspect of the present invention, according to any one of the first to ninth aspects, the stent preferably comprises a core structure of a bioabsorbable material comprising a plurality of cell units, each of the cell units comprising a group of first cells and a group of second cells arranged to oppose each other, wherein the group of first cells includes a plurality of first cells connected to each other, and each of the first cells has two substantially linear parts and a substantially circular-arc part so as to have a substantially U-shaped form which opens toward one end along the axis direction, the group of second cells includes a plurality of second cells connected to each other, each of the second cells is opposed to each of the first cells and has a same shape as the opposed first cell; the opposed groups of cells in the cell unit include two opposed top cells and two opposed bottom cells, both of which being longer than other cells, the top cells being connected with each other as well as the bottom cells being connected with each other to form one cell unit; the plurality of the cell units are arranged so as to enclose the central axis of the stent, and the adjacent cell units are connected by a first connecting member between top cells of one cell unit and bottom cells of another cell unit adjacent to the former cell unit to form a tubular unit; a plurality of the tubular units are arranged in the axis direction of the stent; a part of the opposed cells in the plurality of the tubular unit are connected with each other by a second connecting member; each of the connecting parts of the first connecting member and the second connecting member has a curvature radius of 40 to 100 μm; and the cell having a substantially U-shaped form has an arc part with a curvature radius of 60 to 200 μm.

In an eleventh aspect of the present invention, according to a method of producing the stent of the first aspect, the first coating layer and the second coating layer are formed by spray coating of the biodegradable polymer solution containing acetone or tetrahydrofuran as a solvent.

In a twelfth aspect of the present invention, according to the eleventh aspect, after the first coating layer is formed and dried at 50 to 60° C. for 24 hours or longer under vacuum, the second coating layer is preferably formed.

Any combination of at least two constituent elements disclosed in the claims and/or the specification is included in the present invention. In particular, any combination of two or more of the appended claims should be equally construed as included within the scope of the present invention.

Effect of the Invention

According to the first aspect of the present invention, it is possible to obtain a stent in which the core structure can maintain a radial force for at least about one month, possibly beyond (for six months). Moreover, since all of the core structure, the first coating layer, and the second coating layer comprise biodegradable materials, it is possible to obtain a stent being bioabsorbable over one year or longer. Furthermore, a composite of the optimal combination of the first polymer and the second polymer can effectively suppress local corrosion of the core structure.

According to the second aspect of the present invention, the core structure is a bioabsorbable magnesium alloy, and has excellent biocompatibility and mechanical strength. In particular, a magnesium alloy excluding aluminum and rare earth can further improve biocompatibility.

According to the third aspect of the present invention, the total thickness of the coating layers of from 2 to 10 μm enables to achieve equal membrane thickness so that a desirable effect can be exhibited irrespective of individual specificity.

According to the fourth and fifth aspects of the present invention, it is possible to provide a stent that exhibits the intimal thickening inhibition without excessive inhibition in proliferation of vascular endothelial cells. In particular, the intimal thickening inhibitor released gradually from the second coating layer can effectively deter in-stent-restenosis.

According to the sixth aspect of the present invention, the polymer having a number average molecular weight of 30000 g/mol or smaller is easily eluted during use of the stent so that there is a tendency that the stent has difficulty in realization of a desired effect. On the other hand, the polymer having a number average molecular weight exceeding 200000 g/mol has insufficient solvent solubility, so that such a polymer is not suitable for coating method used in the present invention because of the tendency in deteriorated spray coating. The combination of the first coating layer and the second coating layer each having an optimal number average molecular weight enables to inhibit local corrosion of the core structure. Where the first coating layer and the second coating layer have the smooth surface, disorderly local corrosion can be suppressed. Furthermore, the stent can control gradual release of the intimal thickening inhibitor.

According to the seventh aspect of the present invention, by selecting a specific combination of the first polymer and the second polymer, the local corrosion of the core structure can be highly inhibited so that the physical damage of the core structure can be suppressed.

According to the eighth aspect of the present invention, where the copolymer has a copolymerization ratio of caprolactone of less than 20 mol %, such a copolymer is not always in a rubbery state at 37° C. (body temperature), resulting in failing a desired effect. It is preferred that copolymerization ratio of caprolactone of 20 mol % or higher makes it possible to provide a biodegradable polymer having a lower glass transition point.

According to the ninth aspect of the present invention, the stent having any one of the first to eighth aspects can significantly inhibit temporal deterioration in radial force of the core structure in the simulated plasma solution (EMEM+ 10% FBS) at 37° C. under 5% $CO_2$ atmosphere compared with the stent (core structure only) which does not correspond to the present invention or does not have the coating layer according to the present invention.

According to the tenth aspect of the present invention, by enhancing the durability of the stent as well as providing the stent with the connecting part having a specific curvature radius between the first and the second connecting members, it is possible to reduce crack generation at stress risers and the microscopic cavity which arises in a core structure-polymer interface at the time of stent expansion, so that local corrosion of the bioabsorbable materials (magnesium alloy etc.) can be inhibited. That is, if the core structure does not have excellent expansion homogeneity, it is neither possible to form the stent durable to physical change during the diameter reduction and diameter expansion of the stent, nor possible to maximize the desired effect achieved by the first coating layer and the second coating layer.

According to the eleventh aspect of the present invention, it is preferred that a biodegradable polymer solution can be uniformly applied to all the surface of the core structure by spray coating. Where the first coating layer is firmly adhered to the second coating layer, the bioabsorption rate of the core structure can be reduced.

According to the twelfth aspect of the present invention, by carrying out dry treatment after forming the first coating layer, that is, before forming the second coating layer, for 24 hours or longer at 50 to 60° C. under vacuum, it is possible to smoothen surfaces of the first coating layer as well as the second coating layer, so that disorderly local corrosion can be suppressed.

BRIEF DESCRIPTION OF THE DRAWINGS

This invention will be more clearly understood from the following description of preferred embodiments with reference to the attached drawings. However, the embodiments and the drawings are given only for the purpose of illustration and explanation, and should not be used to limit the scope of the invention. The scope of the invention is determined by the appended claims. In an accompanying drawing, the same reference number in a plurality of drawings shows the same portion.

DESCRIPTION OF THE EMBODIMENTS

Basic Structure of Stent

Figure 1:
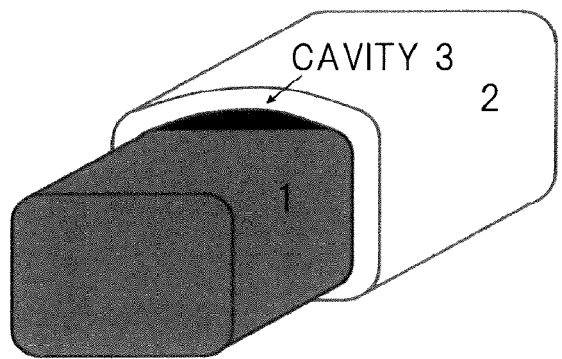
FIG. 1 is a schematic view showing high sealed cavity at a stress riser in the core structure-polymer interface.
Figure 2:
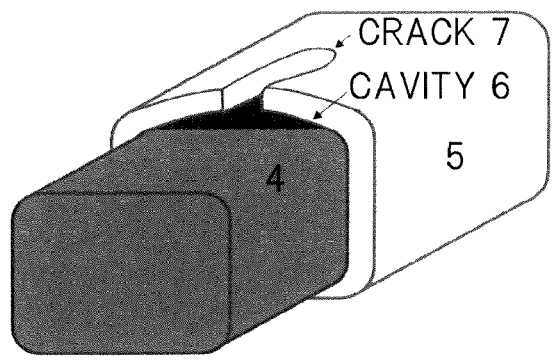
FIG. 2 is a schematic view showing the crack of the polymer caused at the stress riser.

In the first aspect of the present invention, the stent comprises a core structure of a bioabsorbable material, a first coating layer of a biodegradable polymer (a first polymer) which covers the whole surface of the core structure, and a second coating layer of a biodegradable polymer (a second polymer) which covers a part or the whole surface of the first coating layer. The second coating layer may contain an intimal thickening inhibitor in a microdispersed way.

In order to prevent physical damage of the core structure, the first aspect includes a factor for selecting a bioabsorbable material to form the core structure, a factor for coating the core structure with a first polymer and further a second polymer, in addition, a factor for selecting the combination of the first polymer and the second polymer, a factor for selecting Tgs and film thicknesses of the first polymer and the second polymer, respectively, and a factor for controlling a surface shape of the biodegradable polymer.

Core Structure

The core structure of the stent of the present invention comprises a bioabsorbable material. There may be exemplified as biodegradable metals, such as pure magnesium, magnesium alloy, pure iron, and an iron alloy, and preferably magnesium alloy. Furthermore, in respect of safety to human body, a magnesium alloy excluding aluminum and rare earth (Sc, Y, Dy, Sm, Ce, Gd, or La) is still more suitable.

First Polymer

The local corrosion on the surface of the core structure (particularly magnesium alloy) can be suppressed by forming a composite of a first polymer and a second polymer in one of the above-mentioned conditions. That is, it is important for the composite to have an effect to impede local corrosion of the core structure. Even though the first polymer singly has a barrier function to impede contact of water molecules to the core structure, the inhibitory effect by the single first polymer is not sufficient.

As the first polymer used in the present invention, there may be mentioned a poly(L-lactic acid) (PLLA), a poly(D, L-lactic acid) (PDLLA), a polylactic acid-glycolic acid (PLGA), a polyglycolic acid (PGA), a polycaprolactone (PCL), a poly(lactic acid-ε-caprolactone) (PLCL), a polyglycolic acid-ε-caprolactone (PGCL), and a poly(p-dioxanon), a poly(glycolic acid-trimethylenecarbonate), a poly(β-hydroxybutyric acid), and the like. These polymers may be used singly or in combination. Where the number average molecular weight of these polymer is generally comparable, since the PCL (−65° C.≤Tg≤−60° C.) and the PLCL (−60° C.≤Tg≤37° C.) are excellent in pliability and/or ductility at 37° C. as well as in hydrophobicity compared with other polymers, these polymers are suitable as the first polymer. In addition, as long as the PLCL has a Tg of lower than 37° C., the PLCL may not be limited to either a block copolymer or a random copolymer, it is preferred that the copolymerization ratio of caprolactone is 20 mol % or higher. Where the copolymerization ratio of caprolactone is lower than 20 mol %, the copolymer cannot always exhibit rubbery nature at 37° C. so as to fail to realize the desired effect.

Second Polymer

The second polymer desirably controls the eluting rate of the intimal thickening inhibitor supported in the second polymer in addition to the composite effect. As the second polymer used in the present invention, there may be mentioned a poly(L-lactic acid) (PLLA), a poly(D, L-lactic acid) (PDLLA), a polyl(actic acid-glycolic acid) (PLGA), a polyglycolic acid (PGA), a poly(ε-caprolactone) (PCL), a poly(lactic acid-ε-caprolactone) (PLCL), a poly(glycolic acid-ε-caprolactone) (PGCL), a poly(p-dioxanon), a poly (glycolic acid-trimethylenecarbonate), a poly (β-hydroxybutyric acid), and the like. These polymers may be used singly or in combination. In order to control an eluting rate of an intimal thickening inhibitor supported in the second polymer, it is preferred that the second polymer is in a glass state at 37° C. and has a low water content. According to the present invention, it is required that difference in Tg between the first polymer and the second polymer is at least 10° C. or greater. Accordingly, among the above mentioned biodegradable polymers, biodegradable polymers having a glass transition point of 47° C. or higher, such as a PLLA (60° C.≤Tg≤65° C.) and a PDLLA (50° C.≤Tg≤60° C.), are preferably used. In view of a desired medicine elution, each of these polymers may have an arbitrarily adjusted number average molecular weight and/or may form a film having an arbitrarily adjusted film thickness.

Combination of First Polymer and Second Polymer

The second polymer forms a composite via an adhesion surface with the first polymer so as to inhibit physical damage of the core structure. In particular, in order to achieve the preferable object of the present invention, the specific combination of the first polymer and the second polymer serves as an important key.

For example, where a PDLLA is selected as the second polymer, a PLCL is set to one of the choices as the first polymer. The PDLLA forms a composite with the PLCL so as to effectively control the physical damage of the core structure. The PLCL has favorable stent-expansion followability so that the PLCL neither generates cracks at a stress riser, nor generates microscopic cavities in an interface with the core structure. Accordingly, the local corrosion can be suppressed by evasion of local pH rise. On the other hand, a structure in which the upper and lower layers are reversed, that is, the structure comprising a PDLLA as the first polymer and a PLCL as the second polymer adversely causes deterioration in physical properties because the PDLLA cannot follow stent expansion, resulting in generation of local corrosion. Thus, the optimal combination of the first polymer and the second polymer enables to exhibit a desired effect.

As a preferable combination of the first polymer and the second polymer (the first polymer/the second polymer), there may be mentioned PCL (−65° C.≤Tg≤−60° C.)/PDLLA (50° C.≤Tg≤55° C.); PLCL (−60° C.≤Tg≤37° C.)/PDLLA (50° C.≤Tg≤55° C.); PCL (−65° C.≤Tg≤−60° C.)/PLLA (60° C.≤Tg≤65° C.); or PLCL (−60° C.≤Tg≤37° C.)/PLLA (60° C.≤Tg≤65° C.), and the like. Furthermore, by optimizing each of the polymers in view of number average molecular weights and film thicknesses, it is possible to maximize the desired effect.

In the above combinations, where the second polymer forms a composite via an adhesion surface with the first polymer, the second polymer can exhibit the effect to inhibit the physical damage of the core structure.

The first polymer or the second polymer may be constituted by a single polymer or combination of a plurality of polymers (polymer blend) within the range of each of the glass transition point.

Glass Transition Point

It is required for the first polymer to have a Tg of lower than 37° C., and for the second polymer to have a Tg of 47° C. or higher. Where the second polymer has a Tg of lower than 47° C., the composite of the first polymer and the second polymer will be in a rubbery state at 37° C. As a result, even if the composite is able to follow physical change during diameter reduction and diameter expansion, the composite cannot satisfy the function to control the eluting rate of the intimal thickening inhibitor carried by the second polymer. Moreover, where the second polymer has a Tg of 37° C. or higher and lower than 47° C., likewise the composite as mentioned above, the composite of the first polymer and the second polymer will be in a rubbery state at 37° C. As a result, the composite cannot satisfy the function to control the drug-eluting rate. In order to obtain the function, it is suitable for the second polymer to have a Tg of higher by at least 10° C. than the working temperature (37° C.) of the stent. It is preferred that difference in Tg between the first polymer and the second polymer is at least 10° C. or greater. The larger the difference is, the more preferable the combination is.

Crystallinity

The first polymer and the second polymer are not limited to have a specific crystallinity, and may be semicrystalline or crystalline. (Here, the term crystallinity refers to a degree of regular arrangement of the polymer chains. For example, the polymer aggregate comprising single polymer chains has excellent crystallinity.) That is, if the first polymer is in a rubbery state at 37° C., regardless of semicrystalline or crystalline state of the first polymer, it is expectable for the first polymer to achieve a desired effect. As to the second polymer, where the second polymer is in a glass state (Tg: 47° C. or higher) at 37° C., has difference in Tg of higher by at least 10° C. than that of the first polymer; and satisfies the function which controls the eluting rate of the intimal thickening inhibitor, crystallinity of the second polymer is not specifically limited.

Number Average Molecular Weight

It is desirable for each of the first polymer and the second polymer to have a number average molecular weight of from 30000 g/mol to 200000 g/mol, and more preferably from 50000 g/mol to 150000 g/mol. Where each of the polymers has a number average molecular weight of less than 30000 g/mol, there is a tendency that a desired effect is hard to be exhibited. Where each of the polymers has a number average molecular weight of exceeding 200000 g/mol, there is a tendency that such a polymer may not be suitably applied using the coating method according to the present invention.

Film Thickness

It is preferable that each of the first coating layer and the second coating layer has a film thickness of 1 to 5 μm, and/or that the total thickness of the both layers is 10 μm or smaller. More preferably, the first coating layer has a film thickness of 1 to 2 μm, and the second coating layer has a film thickness of 1 to 4 μm, and the total thickness of the both layers is 6 µm or smaller. In addition, it is preferred that the first coating layer and the second coating layer may be prepared to form smooth surface.

Intimal Thickening Inhibitor

If necessary, an intimal thickening inhibitor may be added to the second coating layer. As the intimal thickening inhibitor there may be mentioned sirolimus, everolimus, biolimus A9, zotarolimus, paclitaxel, and the like. In addition, the second coating layer is preferably prepared to have a desired film thickness where the intimal thickening inhibitor is supported.

Coating Layer Formation

In order to form the first coating layer and the second coating layer, the spray coating of a biodegradable polymer solution containing acetone or tetrahydrofuran as a solvent is preferably used. In the spray coating, the biodegradable polymer solution is preferably uniformly applied to all the surfaces of a core structure. During the coating application, it is preferred to adjust viscosity of the polymer solution so that the biodegradable polymer solution can be applied on an arc part of a substantially U-shaped cell. After forming the first coating layer, i.e., before forming the second coating layer, it is preferred to carry out drying process for 24 hours or longer at 50 to 60° C. under reduced pressure.

Coating application and following drying treatment make the first coating layer and the second coating layer to form a composite having excellent adhesion interface. This is effective for preventing unexpected local corrosion as well as medicine elution.

Smooth Surface of Coating Layer

By carrying out the above-mentioned coating application, the second coating layer with smooth surface can be formed on the first coating layer. It is effective for controlling generation of disorderly local corrosions.

Stent Performance

As mentioned above, the stent comprising the first coating layer and the second coating layer can significantly inhibit temporal deterioration in radial force of the core structure in the simulated plasma solution (EMEM+10% FBS) at 37° C. under 5% $CO_2$ atmosphere (refer to the below-mentioned Examples and Comparative Examples) in comparison with the stents which are outside the scope of the present invention or the stent without coating layer (bare core structure).

Stent Scaffold Shape

In the present invention, conventionally known various shapes can be used as stent scaffold shapes. Among them, by forming a tubular unit consisting of a plurality of cell units in which each of the cell units comprises opposed groups of a first cell group and a second cell group, and top cells and bottom cells of the adjacent cell unit are connected with a first connecting member, and by connecting some of the cell units with corresponding second connecting members, the stress and strain applied to the cells are uniformly distributed, resulting in improved durability against bending load without spoiling flexibility of the stent.

According to the present invention, the stent may be an all-linked stent in which all of the opposed cells and links are connected (all-linked stent), or a partially linked stent in which opposed cells and links are partially connected (partially-linked stent).

Figure 3:
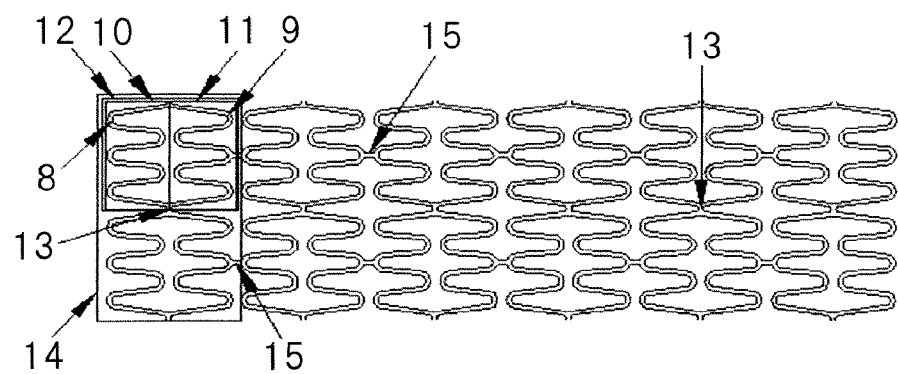
FIG. 3 is a plan view showing an example of the scaffold structure of the stent according to the present invention.

FIG. 3 shows a plan view showing an example of the preferable stent according to the present invention. The stent comprises a first group 10 of first cells 8 and a second group 11 of second cells 9 arranged to oppose each other. Each of the first cells 8 has a substantially U-shaped form which opens toward one end along the axis direction. Each of the second cells 9 is opposed to each of the first cells 8 and has a same shape as the opposed first cell 8. The opposed groups 10, 11 of cells include two opposed top cells and two opposed bottom cells, and the top cells are connected with each other as well as the bottom cells are connected with each other to form one cell unit 12. The first cell unit 12, the second cell unit 12', the third cell unit 12" ... are arranged in a circumferential direction of the stent in this order. The adjacent two cell units, for example, the first cell unit 12 and the second cell unit 12' adjacent with each other, the second cell unit 12' and the third cell unit 12" adjacent with each other, are connected by a first connecting member 13 between top cell part of one cell unit and bottom cell part of another cell unit adjacent to form a tubular unit 14. A plurality of the tubular units 14 are arranged in the axis direction of the stent; only a part of the opposed cells in the plurality of the tubular unit 14 are connected with each other with a second connecting member 15 (partially-linked stent).

Coating Structure of Stent

Figure 4:
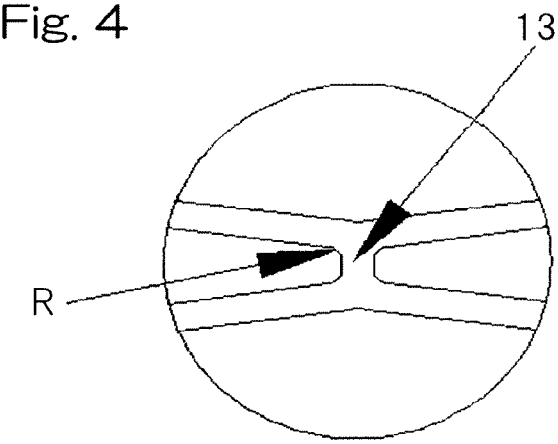
FIG. 4 is a detail view of a connecting part of the first connecting member. The connecting part connects top cells of a cell unit and bottom cells of a cell unit adjacent to the former cell unit.
Figure 5:
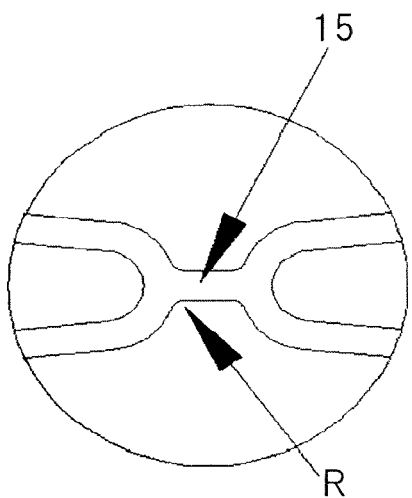
FIG. 5 is a detail view of a connecting part of the second connecting member in which some cells among a plurality of the tubular unit facing with each other are connected with the connecting part.

FIGS. 4 and 5 show detail views of the first connecting member 13 and the second connecting member 15, respectively. Each of the connecting part of the first connecting member 13 and the second connecting member 15 preferably has a curvature radius of 40 to 100 µm; and the cell having a substantially U-shaped form has an arc part with a curvature radius of 60 to 200 µm. The second connecting member 15 that connects the second tubular unit 14' with the first tubular unit 14 is arranged in a line along the axis direction with the second connecting member 15' that connects the adjacent tubular units 14" and 14". Each of the first cell group 10 and the second cell group 11 usually consists of 3 to 5 cells. In order to uniformly distribute stress and strain loaded on cells, the number of cells is usually 3.

Where each of the connecting parts of the first connecting member 13 and the second connecting member 15 has too small curvature radius, the coating polymer may not be applied on the edge so that there is a possibility to generate cavities. If cracks are generated from the cavities in the coating layer, blood intruded into the stent from the cavities brings into contact with a bioabsorbable metal so as to generate corrosion. Where the curvature radius is too large, stress generated at the boundary between the linear part and the substantially circular-arc part in the connecting part may destroy the durability of the stent. Each of the connecting parts of the first connecting member and the second connecting member has a curvature radius of 40 to 100 µm.

If the circular-arc constituting the substantially circular-arc part of cells has too small curvature radius, the coating polymer may not be applied on top surface of the substantially circular-arc part so as to generate cavities, or the coating surface on top of the substantially circular-arc part may cause a crack. If the curvature radius is too large, stress generated at boundary between the linear part and the substantially circular-arc part of the cell may destroy the durability of the stent. The circular-arc constituting the substantially circular-arc part of cell preferably has a curvature radius of 60 to 200 µM.

Stent Basic Structure

Figure 6:
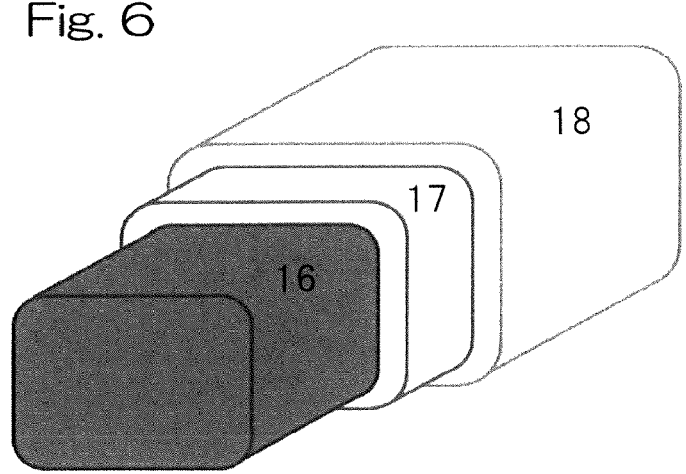
FIG. 6 is a schematic view showing the components of the stent according to the present invention.

An example of the basic structure of the stent according to the present invention is shown in FIG. 6.

The stent according to the present invention comprises (a) a core structure 16 of a bioabsorbable magnesium alloy, (b) a first coating layer 17 of a first polymer that covers the whole surface of the core structure, and (c) a second coating layer of a second polymer 18 which covers a part or the whole surface of the first coating layer. In order to exhibit effect to suppress generation of disorderly local corrosion of the core structure by forming a composite in which the second polymer adheres to the first polymer via an adhesion surface, it is preferred that the first coating layer and the second coating layer may form the smooth surface.

Polymer Constituting First Coating Layer and Second Coating Layer

Since the stent of the present invention is bioabsorbable, biodegradable polymer needs to be used. As examples of the biodegradable polymer, there may be mentioned a poly(L-lactic acid) (PLLA), a poly(D,L-lactic acid) (PDLLA), a poly(lactic acid-glycolic acid) (PLGA), a polyglycolic acid (PGA), a polycaprolactone (PCL), a poly(lactic acid-ε-caprolactone) (PLCL), a poly(glycolic acid-ε-caprolactone) (PGCL), a poly(p-dioxanon), a poly(glycolic acid-trimethylenecarbonate), a poly(6-hydroxybutyric acid), and the like. As for the second polymer, since the second polymer may have a function to support an intimal thickening inhibitor, it is preferred that the second polymer is in a glass state above 37° C., and has a low water content. Accordingly, the PLLA and the PDLLA are more preferred among above mentioned biodegradable polymers.

Each of the first polymer and the second polymer suitably has a number average molecular weight of 30000 g/mol to 200000 g/mol. There is a tendency that the polymer having a number average molecular weight of less than 30000 g/mol may be hard to exhibit desired effect. On the other hand, the polymer having a number average molecular weight exceeding 200000 g/mol is not suitable for the coating method used in the present invention. In the below-mentioned Examples and Comparative Examples, the PLCL with a number average molecular weight of 50000 g/mol was selected as the first polymer, and the PDLLA with a number average molecular weight of 50000 g/mol was selected as the second polymer.

Film Thicknesses of First and Second Coating Layers

Each of the first coating layer and the second coating layer of the stent according to the present invention preferably has a film thickness of 1 to 5 μm. If the coating layer has a thickness of less than 1 μm there is a tendency that applying the coating solution to the whole region of core structure becomes difficult. On the other hand, if the coating layer has a thickness exceeding 5 μm, there is a tendency that that the uniformity on film thickness as well as the surface structure may be hard to be achieved so that a desired effect may be spoiled. In the below-mentioned Examples and Comparative Examples, each of the first coating layer and the second coating layer is selected to have a film thickness of about 2 μm.

Preparing Method of First Coating Layer and Second Coating Layer

As a method for forming the first coating layer and the second coating layer, there may be mentioned a dipping method in which a subject is immersed into a coating solution containing components constituting each of the coating layer, a spraying method in which a liquid mist of a coating solution is sprayed to a subject, a double simultaneous spraying method in which separate coating solutions are sprayed simultaneously from two spinnerets, and others. In the spray coating, acetone or tetrahydrofuran may be preferably used as a solvent. It should be noted that after forming the first coating layer, i.e., before forming the second coating layer, it is desirable to add the drying process for 24 hours or longer at 50 to 60° C. under vacuum. With the preparing method, the surfaces of the first coating layer and the second coating layer can be smoothed so as to suppress generation of disorderly local corrosions.

As mentioned above, according to the present invention, the first coating layer and the second coating layer are formed on the core structure, and the composite of the first coating layer and the second coating layer can attain a desired effect.

EXAMPLES

Hereinafter, the present invention will be described by referring to Example in detail. It should be noted that the present invention be not limited to the following Examples.

Each of the stents used in Examples according to the present invention has a structure shown in FIG. 6. The stents used in Comparative Examples 1 to 4 have the structures shown in FIG. 7 to FIG. 10, respectively. The stent shown in FIG. 7 comprises the core structure 19 of a bioabsorbable magnesium alloy, the first coating layer 20 of the first polymer having a Tg over 37° C., and the second coating layer 21 of the second polymer. The stent shown in FIG. 8 comprises the core structure 22 of a bioabsorbable magnesium alloy, the first coating layer 23 of the first polymer, and the second coating layer 24 of a second polymer completely same as the first polymer. The stent shown in FIG. 9 comprises the core structure 25 of a bioabsorbable magnesium alloy and only the coating layer 26 of the first polymer that covers the whole surface of the core structure 25 without providing second coating layer. The stent shown in FIG. 10 comprises the core structure 27 of a bioabsorbable magnesium alloy without providing first and second coating layers.

Corrosion-Resistant Evaluation Method

In the present test, as shown below, a core structure was formed from bioabsorbable magnesium alloy AZ31, and then samples were prepared in accordance with the below-mentioned Examples and Comparative Examples. Each sample was evaluated regarding corrosion resistance of the core structure.

Figure 11:
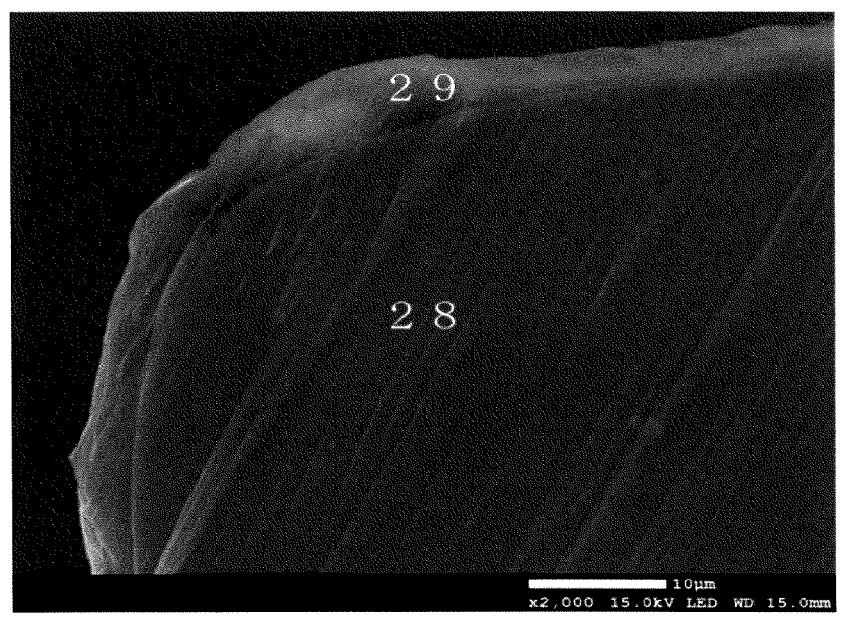
FIG. 11 is a SEM photograph image of the core structure surface of the stent according to the present invention used for the corrosion resistance test.
Figure 12:
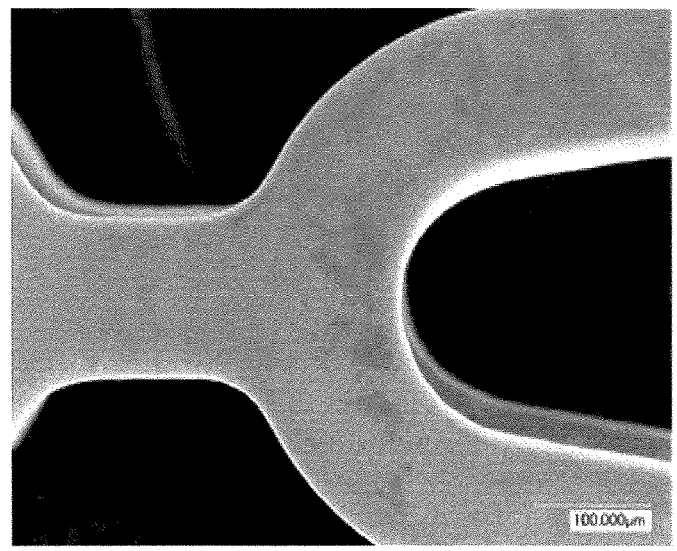
FIG. 12 is a SEM photograph image of a cross section of the stent according to the present invention used for the corrosion resistance test.

After producing a scaffold (core structure) having a shape shown in FIG. 3 by laser processing, the scaffold was electrolytic-polished so as to obtain a core structure with 1.8 mm of outer diameter, 18 mm in length, 120 μm in thickness, 103.8 $mm^2$ in surface area, and 5 mg in weight. The core structure had a shape shown in FIG. 11. Each of the samples prepared in accordance with Examples and Comparative Examples was expanded to have an inner diameter of 3 mm in 37° C. simulated plasma solution (EMEM+10% FBS), and was shaken at 100 rpm with keeping immersion at 37° C. under 5% $CO_2$ atmosphere. The samples were taken out at 28 days after immersion, and the radial force of each of the samples was measured (n=4) with SEM observation of the surface (n=1). Further, the sample was cleaned ultrasonically with a tetrahydrofuran (THF) and chromic acid so that the corrosion product of coating polymer, magnesium hydroxide, etc. were removed completely, and the weight change of the core structure was evaluated (n=5). As to the radial force measurement, RX550/650 (Machine Solutions) were used.

Example 1

Spray coating of the first polymer PLCL at an amount of 200±20 μg per stent as the first coating layer and spray coating of the second polymer PDLLA at an amount of 200±20 μg per stent as the second coating layer were carried out on the surface of the core structure and the surface of the first coating layer, respectively to prepare a stent sample shown in FIG. 6 (thickness of the first coating layer: about 2 μm, thickness of the second coating layer: about 2 μm).

First, after polishing the core structure, the core structure was mounted on a mandrel of a spray type coating apparatus at 9 mm below the spinneret and reciprocatingly moved at a rate of 120 rpm together with the mandrel. Then, a 1% PLCL coating solution in tetrahydrofuran (THF) was applied for about 120 seconds at a spraying rate of 0.02 mL/min. to a surface of the core structure ranging from one end thereof to an intermediate portion thereof so as to coat a half surface of the core structure. Then, after drying the core structure for 3 minutes at 60° C. under vacuum, the remaining half surface of the core structure was coated. The whole coated sample was dried at 60° C. for 24 hours under vacuum, a 1% PDLLA coating solution was applied to the PLCL-coated core structure in the same way as described above. At the end, ethylene oxide gas (FOG) sterilization was performed to the prepared sample. A total of five samples were prepared on the same conditions as this condition.

Example 1 is an exemplary stent based on the present invention. The whole surface of the core structure of a bioabsorbable magnesium alloy is coated with the PLCL (Tg: about 20° C.) as the first polymer, and further covered with the PDLLA (Tg: about 55° C.) as the second polymer.

The SEM photograph image (FIG. 11) of the cross-sectional sample revealed that the interface between the core structure and the first polymer was recognized (The image here shows an Mg alloy layer 28 and a coating layer 29 in which the first coating layer and the second coating layer were integrated). On the contrary, the interface between the first coating layer and the second coating layer was not visually recognized because a composite was formed between the first coating layer and the second coating layer.

Comparative Example 1

Figure 7:
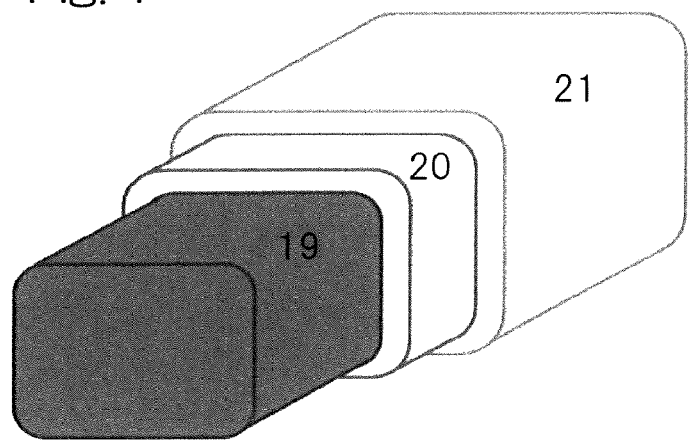
FIG. 7 is a schematic view of Comparative Example 1 showing comparison with the components of the stent according to the present invention.

Spray coating of the PDLLA at an amount of 200±20 μg per stent as the first coating layer and spray coating of the PLCL at an amount of 200±20 μg per stent as the second coating layer were carried out on the surface of the core structure and the surface of the first coating layer, respectively to prepare a stent sample shown in FIG. 7.

First, after polishing the core structure, the core structure was mounted on a mandrel of a spray type coating apparatus at 9 mm below the spinneret and reciprocatingly moved at a rate of 120 rpm together with the mandrel. Then, a 1% PDLLA coating solution in THF was applied for about 120 seconds at a spraying rate of 0.02 mL/min. to a surface of the core structure ranging from one end thereof to an intermediate portion thereof so as to coat a half surface of the core structure. Then, after drying the core structure for 3 minutes at 60° C. under vacuum, the remaining half surface of the core structure was coated. The whole coated sample was dried at 60° C. for 24 hours under vacuum, a 1% PLCL coating solution was applied to the PDLLA-coated core structure in the same way as described above. At the end, ethylene oxide gas (EOG) sterilization was performed to the prepared sample. A total of five samples were prepared on the same conditions as this condition.

As shown in FIG. 7, the obtained sample consists of (a) the core structure 19 of the bioabsorbable magnesium alloy, (b) the first coating layer 20 of the first polymer (PDLLA) coating the whole surface of the core structure, and (c) the second coating layer 21 of the second polymer (PLCL). This aspect is outside the scope of the present invention because Tg of the first polymer is 37° C. or higher and Tg of the second polymer is lower than 37° C.

Comparative Example 2

Figure 8:
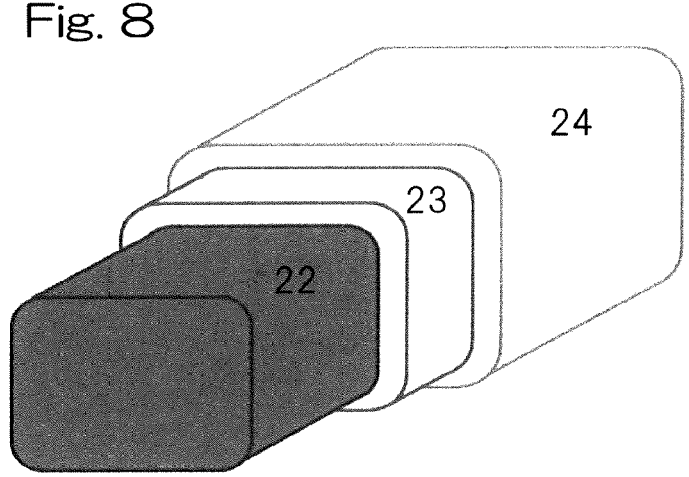
FIG. 8 is a schematic view of Comparative Example 2 showing comparison with the components of the stent according to the present invention.

Spray coating of the PDLLA at an amount of 200±20 μg per stent as the first coating layer and spray coating of the same PDLLA as the first coating layer at an amount of 200±20 μg per stent as the second coating layer were carried out on the surface of the core structure and the surface of the first coating layer, respectively to prepare a stent sample shown in FIG. 8.

First, after polishing the core structure, the core structure was mounted on a mandrel of a spray type coating apparatus at 9 mm below the spinneret and reciprocatingly moved at a rate of 120 rpm together with the mandrel. Then, a 1% PDLLA coating solution in THF was applied for about 120 seconds at a spraying rate of 0.02 mL/min. to a surface of the core structure ranging from one end thereof to an intermediate portion thereof so as to coat a half surface of the core structure. Then, after drying the core structure for 3 minutes at 60° C. under vacuum, the remaining half surface of the core structure was coated. The whole coated sample was dried at 60° C. for 24 hours under vacuum, the same solution was applied to the PDLLA-coated core structure in the same way as described above. At the end, ethylene oxide gas (EOG) sterilization was performed to the prepared sample. A total of five samples were prepared on the same conditions as this condition.

As shown in FIG. 8, the obtained sample consists of (a) the core structure 22 of the bioabsorbable magnesium alloy, (b) the coating layer 23 of the first polymer (PDLLA) coating the whole surface of the core structure, and (c) the coating layer 24 of the second polymer PDLLA) that is same with the first polymer. This aspect is outside the scope of the present invention because Tg of the first polymer is 37° C. or higher.

Comparative Example 3

Figure 9:
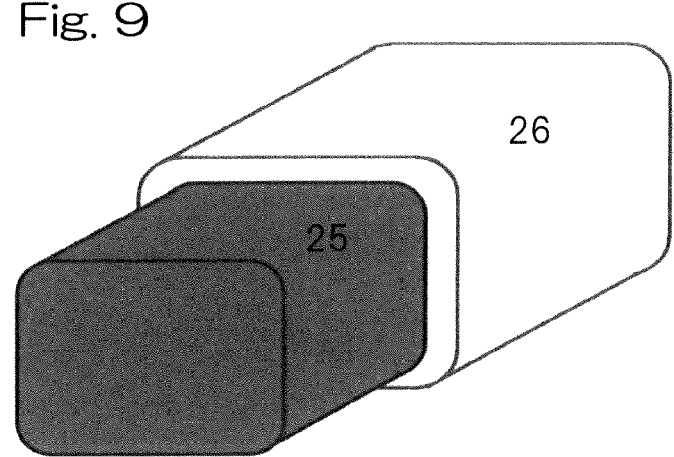
FIG. 9 is a schematic view of Comparative Example 3 showing comparison with the components of the stent according to the present invention.

One time spray coating of the PDLLA at an amount of 200±20 μg per stent as the first coating layer was carried out on the surface of the core structure to prepare a stent sample shown in FIG. 9.

First, after polishing the core structure, the core structure was mounted on a mandrel of a spray type coating apparatus at 9 mm below the spinneret and reciprocatingly moved at a rate of 120 rpm together with the mandrel. Then, a 1% PDLLA coating solution in TI IF was applied for about 120 seconds at a spraying rate of 0.02 mL/min. to a surface of the core structure ranging from one end thereof to an intermediate portion thereof so as to coat a half surface of the core structure. Then, after drying the core structure for 3 minutes at 60° C. under vacuum, the remaining half surface of the core structure was coated. The whole coated sample was dried at 60° C. for 24 hours under vacuum. At the end, ethylene oxide gas (EOG) sterilization was performed to the prepared sample. A total of five samples were prepared on the same conditions as this condition.

As shown in FIG. 9, the obtained sample consists of (a) the core structure 25 of the bioabsorbable magnesium alloy, and (b) the first coating layer 26 of the first polymer (PDLLA) coating the whole surface of the core structure.

Comparative Example 4

Figure 10:
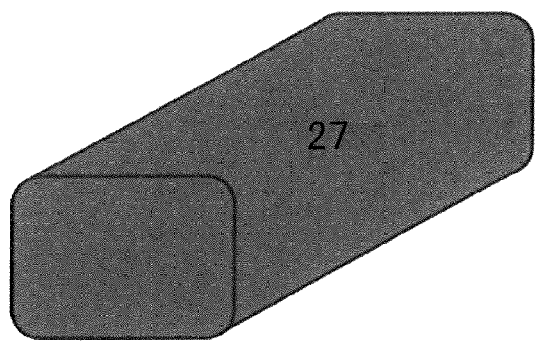
FIG. 10 is a schematic view of Comparative Example 4 showing comparison with the components of the stent according to the present invention.

Ethylene oxide gas (EOG) sterilization was performed to a sample of polished core structure. As shown in FIG. 10, the obtained sample consists of (a) the core structure 27 of the bioabsorbable magnesium alloy. A total of five samples were prepared on the same conditions as this condition.

The formulations of the samples obtained in Example and Comparative Examples 1 to 4 are shown in Table 1. As the PLCL, a random copolymer (caprolactone-copolymerization ratio of 20 mol %) (produced by DURECT) having a number average molecular weight of 50000 g/mol was used. As the PDLLA, a random copolymer (D-body-polymerization ratio of 50 mol %) (produced by DURECT) having a number average molecular weight of 50000 g/mol was used.

TABLE 1

Components of stents in Example 1 and Comparative Examples 1 to 4

| | Core Structure | First Coating Polymer | Second Coating Polymer |
|---|---|---|---|
| Example 1 FIG. 6 | Mg alloy 120 μm | PLCL 2 μm | PDLLA 2 μm |
| Com. Ex. 1 FIG. 7 | Mg alloy 120 μm | PDLLA 2 μm | PLCL 2 μm |
| Com. Ex. 2 FIG. 8 | Mg alloy 120 μm | PDLLA 2 μm | PDLLA 2 μm |
| Com. Ex. 3 FIG. 9 | Mg alloy 120 μm | PDLLA 2 μm | — |
| Com. Ex. 4 FIG. 10 | Mg alloy 120 μm | — | — |

Weight Change of Core Structure Before and after Immersion

The core structure weights of each of the samples before immersion as well as at 28 days after immersion in the simulated plasma solution were measured. Table 2 shows the result of the weight residual ratio of the core structure before and after immersion calculated based on the weight of the core structure before immersion. The weight of the core structure before immersion was 5.85 mg.

TABLE 2

Weight Change of Core Structure Before And After Immersion (Weight Residual Ratio [%])

| | Before immersion | 28 Days After Immersion | Remarks |
|---|---|---|---|
| Example 1 | 100 | 84.9 ± 3.4 | FIG. 6 |
| Com. Ex. 1 | 100 | 26.6 ± 8.5 | FIG. 7 |
| Com. Ex. 2 | 100 | 25.1 ± 9.0 | FIG. 8 |
| Com. Ex. 3 | 100 | 24.6 ± 5.5 | FIG. 9 |
| Com. Ex. 4 | 100 | 42.6 ± 9.1 | FIG. 10 |

Relative Evaluation of Stent at 28 Days after Immersion

Figure 13:
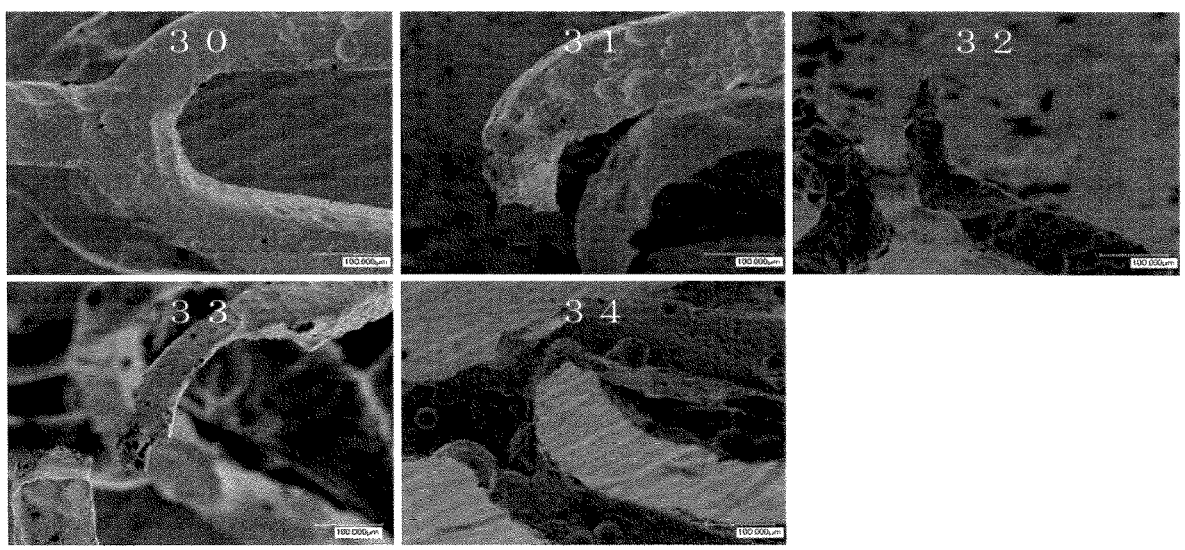
FIG. 13 is a SEM photograph image of the core structure surface at 28 days after the corrosion resistance test.

The sample (Example 1) with components based on the present invention had significantly high weight residual ratio compared with the comparison samples (Comparative Example 4) so as to be presumed that the coating layers inhibit corrosion. Further, the comparison samples (Comparative Examples 1 to 3) outside the scope of the present invention ended up unmeasurable intense damage triggered by accelerative corrosion. As shown in FIG. 13, it was observed that although some marks of corrosion were observed in some points, the core structure of Example 1 (FIG. 13-30) maintained the stent shape. On the other hand, the core structures of Comparative Example 1 (FIG. 13-31), Comparative Example 2 (FIG. 13-32), Comparative Example 3 (FIG. 13-33), and Comparative Example 4 (FIG. 13-34) were affected by much faster corrosion, and severe damage (fracture) in shape was observed. Accordingly, it was suggested that the sample (Example 1) which had components based on the present invention exhibited the significant corrosion impedance effect compared with all the comparison samples (Comparative Examples 1 to 4).

Change in Physical Properties of Core Structure Before and after Immersion

The core structure radial force of each of the samples before immersion as well as at 28 days after immersion in a simulated plasma solution was measured. Table 3 shows the result of the radial force residual ratio of the core structure before and after immersion calculated based on the radial force of the core structure before immersion. The radial force of the core structure before immersion was 63.525 N/mm.

TABLE 3

Change in Physical Properties of Core Structure Before and After Immersion (radial force residual ratio [%])

| | Before immersion | 28 Days After Immersion | Remarks |
|---|---|---|---|
| Example 1 | 100 | 67.3 ± 4.1 | FIG. 6 |
| Com. Ex. 1 | 100 | 0 | FIG. 7 |
| Com. Ex. 2 | 100 | 0 | FIG. 8 |
| Com. Ex. 3 | 100 | 0 | FIG. 9 |
| Com. Ex. 4 | 100 | 0 | FIG. 10 |

Relative Evaluation of Samples at 28 Days after Immersion

It was confirmed that the sample (Example 1) with components based on the present invention had a radial force residual ratio of 50% or more thanks to improved corrosion suppression by the composite coating layer. On the other hand, all the comparison samples (Comparative Examples 1 to 4) were subject to faster corrosion, resulting in complete failure of the radial force. That is, in order to achieve the object of the present invention, it can be said that the combination of the first polymer and the second polymer is the most important key. Details are described below.

Comparison with Comparative Example 1

As mentioned above, Example 1 is an embodiment of the exemplary stent based on the present invention. In Example 1, the whole surface of the core structure of the bioabsorbable magnesium alloy is coated with the first polymer of PLCL (Tg: about 20° C.), and further with the second polymer of PDLLA (Tg: about 55° C.). On the other hand, in Comparative Example 1, the first polymer and the second polymer in Example 1 are arranged reversely. Since the PDLLA which is used for coating the surface of the core structure was in a glass state, the PDLLA was unable to follow expansion of the core structure in simulated plasma solution. As a result, it was suggested that occurrence of cracks as the starting point affected the core structure so as to arise damage, resulting in accelerated corrosion. As shown in Tables 2 and 3, both the weight residual ratio and the radial force residual ratio in Example 1 were significantly higher compared with those in Comparative Example 1. Accordingly, the importance fulfilling the condition that "Tg of the first polymer is lower than 37° C." was indicated.

Comparison with Comparative Example 2

As mentioned above, Comparative Example 2 contains PDLLA as the first polymer instead of the first polymer PLCL in Example 1. That is, the first polymer completely comprises the same polymer (PDLLA) with the second polymer. Both the weight residual ratio and radial force residual ratio of Example 1 were significantly higher compared with Comparative Example 2. Accordingly, in order to inhibit local corrosion of core structure, it was suggested that the combination of the first polymer and the second polymer was important.

Comparison with Comparative Example 3

In Comparative Example 3, the first polymer (PLCL) in Example 1 was not coated. The weight residual ratio and the radial force residual ratio in Example 1 were significantly higher compared with those in Comparative Example 3, and it was suggested that existence of the first coating layer (the first polymer) sandwiched between the core structure and the second coating layer (second polymer) was important.

Comparison with Comparative Example 4

Comparative Example 4 does not have a coating layer, i.e., it is a bare core structure. The weight residual ratio and radial force residual ratio in Example 1 are significantly higher than those in Comparative Example 4. That is, it was suggested that the coating layer of Example 1 exhibited the desired effect. Excluding Example 1, the weight residual ratio of Comparative Example 4 is significantly higher compared to those of Comparative Examples 1 to 3, each of which has a coating layer. It is suggested that while the core structures in Comparative Examples 1 to 3 cause local corrosion, the whole surface of the core structure in Comparative Example 4 is uniformly corroded (whole corrosion). Accordingly, it is suggested that the incongruent coating layers outside the scope of the present invention bring about local corrosion, resulting in remarkable damage in physical properties.

Evaluation Method of Drug Elution

In this test, as shown below, a core structure consisting of a CoCr alloy instead of a bioabsorbable magnesium alloy was used because the Mg alloy was more easily affected by corrosion. After producing samples in accordance with Example and Comparative Examples as described below, the drug elution rate was evaluated with respect to the samples on which a drug (sirolimus) was applied together with the biodegradable polymer.

After producing the scaffold shape shown in FIG. 3 by laser processing, core structures each with 1.8 mm in outer diameter, 18 mm in length, 120 μm in thickness, and 103.8 mm² in surface area were obtained by electrolytic polishing. After producing the samples in accordance with the below-mentioned Example and Comparative Examples, each of the sample was expanded into 3 mm in inner diameter in 37° C. PBS, and shaken at 100 rpm under 37° C. with keeping immersion. At 1, 3, 7, 14, 21 and 28 days after immersion, the amount of sirolimus eluted in PBS was quantitatively determined by measuring UV absorption (331 nm) using ultraviolet visible spectrometer, UV-2450 manufactured by SHIMADZU Corporation.

Example 2

Stent samples were prepared by spray-coating of the polymer PDLLA (200±20 μg per stent) containing sirolimus (100±10 μg per stent) on the surface of the core structure. First, after polishing the core structure, the core structure was mounted on a mandrel of a spray type coating apparatus at 9 mm below the spinneret and reciprocatingly moved at a rate of 120 rpm together with the mandrel. Then, a 0.5%/1% sirolimus/PDLLA coating solution in THF was applied for about 120 seconds at a spraying rate of 0.02 mL/min. to a surface of the core structure ranging from one end thereof to an intermediate portion thereof so as to coat a half surface of the core structure. Then, after drying the core structure for 3 minutes at 60° C. under vacuum, the remaining half surface of the core structure was coated. Ethylene oxide gas (EOG) sterilization was performed to the prepared sample. A total of three samples were prepared on the same conditions as this condition.

Comparative Example 5

Stent samples were prepared by spray-coating of the polymer PLCL (200±20 μg per stent) containing sirolimus (100±10 μg per stent) on the surface of the core structure. First, after polishing the core structure, the core structure was mounted on a mandrel of a spray type coating apparatus at 9 mm below the spinneret and reciprocatingly moved at a rate of 120 rpm together with the mandrel. Then, a 0.5%/1% sirolimus/PLCL coating solution in THF was applied for about 120 seconds at a spraying rate of 0.02 mL/min. to a surface of the core structure ranging from one end thereof to an intermediate portion thereof so as to coat a half surface of the core structure. Then, after drying the core structure for 3 minutes at 60° C. under vacuum, the remaining half surface of the core structure was coated. Ethylene oxide gas (EOG) sterilization was performed to the prepared sample. A total of three samples were prepared on the same conditions as this condition.

Comparative Example 6

Except for using the polymer PCL instead of the polymer PLCL in Comparative Example 5, samples were prepared in the same way as Comparative Example 5.

As the PDLLA, a random copolymer (D-body-polymerization ratio of 50 mol %) (produced by DURECT) having a number average molecular weight of 50000 g/mol was used. As the PLCL, a random copolymer (caprolactone-copolymerization ratio of 20 mol %) (produced by DURECT) having a number average molecular weight of 50000 g/mol was used. As the PCL, a homopolymer (produced by DURECT) having a number average molecular weight of 50000 g/mol was used.

Temporal Variation of Eluted Drug Amount after Immersion

The amount of sirolimus eluted in PBS was quantitatively determined at 1, 3, 7, 14, 21 and 28 days after immersion. The drug elution rate was calculated based on the amount of drug applied to the surface of the core structure before immersion. The result is shown in Table 4.

The samples (Example 2) based on the present invention each containing the drug-supporting polymer had significantly lower drug elution rates compared with those in the comparison samples (Comparative Examples 5 and 6) which were outside the scope of the present invention. It was suggested that the drug elution was suppressed by the polymer condition (glass state).

TABLE 4

| | Eluted Drug Amount (%) | | | |
| --- | --- | --- | --- | --- |
| | Immersed Period | | | |
| | Day 1 | Day 3 | Day 7 | Day 14 |
| Example 2 | 35.0 | 39.5 | 54.3 | 55.5 |
| Com. Ex. 5 | 65.7 | 77.5 | 91.9 | 100 |
| Com. Ex. 6 | 82.8 | 96.7 | 100 | 100 |

Although the present invention has been fully described in connection with the preferred embodiments thereof with reference to the accompanying drawings, those skilled in the art will readily conceive numerous changes and modifications within the framework of obviousness upon the reading of the specification herein presented of the present invention. Accordingly, such changes and modifications are to be construed as included therein.

DESCRIPTION OF NOTATIONS 1, 4, 16, 19, 22, 25, 27, and 28: Core structure of magnesium alloy
2, 5, 17, 20, 23, 26: First coating layer of biodegradable polymer
3, 6: Cavity
18, 21, 24: Second coating layer of biodegradable polymer
7: Crack
8: First cell
9: Second cell
10: First cell group
11: Second cell group
12: Cell unit
13: First connecting member
14: Tubular unit
15: Second connecting member
29: Composite of first polymer and second polymer
30, 31, 32, 33, 34: Sample at 28 days after immersion in simulated plasma solution.

What is claimed is:

1. A stent, comprising:
a core structure of a bioabsorbable magnesium alloy;
a first coating layer of a first polymer with biodegradability, the first coating layer covering the whole surface of the core structure and the first polymer having a glass transition point of lower than 37° C.; and
a second coating layer of a second polymer with biodegradability, the second coating layer covering a part or the whole surface of the first coating layer, and the second polymer having a glass transition point of 47° C. or higher,
wherein
a combination of the first polymer and the second polymer is, as combinations of first polymer/second polymer, PCL/PDLLA or PLCL/PDLLA,
a composite is formed between the first coating layer and the second coating layer,
the bioabsorbable magnesium alloy includes a plurality of cell units, each of the cell units among the plurality of cell units including a first group of first cells and a second group of second cells,
adjacent cell units among the plurality of cell units are connected with each other by a first connecting member, the first connecting member extending in a circumferential direction of the stent and having a portion with a curvature radius of 40 μm to 100 μm which is open in an axis direction of the stent,
a plurality of tubular units are arranged in the axis direction of the stent, the plurality of tubular units including a first tubular unit and a second tubular unit, and
a portion of cells of the first tubular unit oppose and are connected with a corresponding portion of cells of the second tubular unit, by a second connecting member, the second connecting member extending in the axis direction of the stent and having a portion with a curvature radius of 40 μm to 100 μm which is open in a circumferential direction of the stent.

2. The stent according to claim 1, wherein each of the first coating layer and the second coating layer has a film thickness of from 1 μm to 5 μm.

3. The stent according to claim 1, wherein the second coating layer of the second polymer contains an intimal thickening inhibitor.

4. The stent according to claim 3, wherein the intimal thickening inhibitor is sirolimus, everolimus, biolimus A9, zotarolimus, and/or paclitaxel.

5. The stent according to claim 2, wherein each of the first polymer and the second polymer has a number average molecular weight of 30000 g/mol to 200000 g/mol.

6. The stent according to claim 2, wherein the PLCL has a copolymerization ratio of caprolactone of 20 mol % or higher.

7. The stent according to claim 2, wherein the core structure of the bioabsorbable magnesium alloy has a radial force maintained over one month in a simulated plasma solution (EMEM+10% FBS) at 37° C. under 5% $CO_2$ atmosphere.

8. The stent according to claim 2, wherein
the first cells are connected to each other, and each of the first cells has two substantially linear parts and a substantially circular-arc part so as to have a substantially U-shaped form which is open toward one end along the axis direction of the stent,
the second cells are connected to each other, and each of the second cells is opposed to a respective first cell among the first cells and has a same shape as the respective first cell,
the first cells include a top cell and a bottom cell,
the second cells include a top cell and a bottom cell,
the top cell of the first cells opposes and is connected with the top cell of the second cells and the bottom cell of the first cells opposes and is connected with the bottom cell of the second cells,
the plurality of cell units are arranged so as to enclose a central axis of the stent,
the adjacent cell units include a first cell unit and a second cell unit,
top cells of the first cell unit are connected to bottom cells of the second cell unit by the first connecting member to form a tubular unit, and
the substantially circular-arc part of each of the first cells has a curvature radius of 60 μm to 200 μm.

9. A method of producing the stent recited in claim 2, wherein each of the first coating layer and the second coating layer are formed by spray coating of a biodegradable polymer solution containing acetone or tetrahydrofuran as a solvent.

10. The method according to claim 9, wherein after the first coating layer is formed and dried at 50° C. to 60° C. for 24 hours or longer under vacuum, the second coating layer is formed.

* * * * *

UNITED STATES PATENT AND TRADEMARK OFFICE
CERTIFICATE OF CORRECTION

PATENT NO. : 11,207,448 B2
APPLICATION NO. : 15/988482
DATED : December 28, 2021
INVENTOR(S) : Makoto Sasaki et al.

It is certified that error appears in the above-identified patent and that said Letters Patent is hereby corrected as shown below:

In the Claims

Column 22, Line 15:
In Claim 5, delete "2," and insert --1,--

Column 22, Line 18:
In Claim 6, delete "2," and insert --1,--

Column 22, Line 21:
In Claim 7, delete "2," and insert --1,--

Column 22, Line 26:
In Claim 8, delete "2," and insert --1,--

Column 22, Line 52:
In Claim 9, delete "2," and insert --1,--

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*